(12) United States Patent
Daerr

(10) Patent No.: US 11,529,111 B2
(45) Date of Patent: Dec. 20, 2022

(54) EXAMINATION OF A BLOOD VESSEL BASED ON NUCLEAR RESONANT ABSORPTION

(71) Applicant: KONINKLIJKE PHILIPS N.V., Eindhoven (NL)

(72) Inventor: Heiner Daerr, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/265,561

(22) PCT Filed: Aug. 6, 2019

(86) PCT No.: PCT/EP2019/071091
§ 371 (c)(1),
(2) Date: Feb. 3, 2021

(87) PCT Pub. No.: WO2020/030627
PCT Pub. Date: Feb. 13, 2020

(65) Prior Publication Data
US 2021/0321967 A1 Oct. 21, 2021

(30) Foreign Application Priority Data
Aug. 7, 2018 (EP) .................................. 18187724

(51) Int. Cl.
*A61B 6/00* (2006.01)
*A61B 6/03* (2006.01)
*A61K 49/04* (2006.01)

(52) U.S. Cl.
CPC .............. *A61B 6/504* (2013.01); *A61B 6/037* (2013.01); *A61B 6/405* (2013.01); *A61B 6/466* (2013.01);
(Continued)

(58) Field of Classification Search
CPC ......... A61B 6/504; A61B 6/037; A61B 6/405; A61B 6/466; A61B 6/481; A61B 6/482;
(Continued)

(56) References Cited

U.S. PATENT DOCUMENTS

| 4,815,447 A | 3/1989 | Mills |
| 7,564,241 B2 | 7/2009 | Barty |

(Continued)

FOREIGN PATENT DOCUMENTS

| CN | 1821866 A | 8/2006 |
| WO | 2009097052 A1 | 8/2009 |

OTHER PUBLICATIONS

PCT International Search Report, International application No. PCT/EP2019071091, dated Nov. 15, 2019.
Friedman et al., "The Effect of Aluminum and pH on Altered Body Distribution egmTc-EHDP", Work in Progress, International Journal of Nuclear Medicine and Biology, 1976, vol. 3(1), pp. 37-40.
(Continued)

*Primary Examiner* — Courtney D Thomas
(74) *Attorney, Agent, or Firm* — Larry Liberchuk

(57) ABSTRACT

The invention relates to a system and a method for determining a characteristic of a blood vessel portion, which comprises blood including a contrast agent exhibiting resonant absorption of x-ray photons at a specific energy. The system comprises a tunable monochromatic x-ray source (21) emitting x-ray radiation, an x-ray detector device (22) for detecting the x-ray radiation after it has travelled through the blood vessel portion. A control unit (26) varies a tuning of the x-ray source (21) to vary the energy of the x-ray radiation emitted by the x-ray source (21), and an evaluation unit (27) determines a tuning of the x-ray source (21) at which nuclear resonant absorption of the x-ray radiation incident onto the blood vessel portion occurs and estimates the characteristic on the basis of the determined tuning. The characteristic may particularly be the blood velocity in the blood vessel portion.

15 Claims, 3 Drawing Sheets

(52) U.S. Cl.
CPC .............. *A61B 6/481* (2013.01); *A61B 6/482* (2013.01); *A61B 6/541* (2013.01); *A61K 49/0438* (2013.01)

(58) Field of Classification Search
CPC ....... A61B 6/541; A61B 6/4258; A61B 6/507; A61B 6/00; A61B 6/4064; A61B 6/5217; A61K 49/0438; A61K 49/0004; A61K 49/04; G01N 23/095; G01N 33/49; G01T 1/26; G01T 1/29; G16H 50/30
See application file for complete search history.

(56) References Cited

U.S. PATENT DOCUMENTS

| | | | |
|---|---|---|---|
| 7,715,528 B2 | 5/2010 | Miura | |
| 2002/0051751 A1 | 5/2002 | Mills | |
| 2002/0057760 A1 | 5/2002 | Carroll | |
| 2013/0294576 A1* | 11/2013 | Pradhan | ............... A61N 5/1027 378/124 |
| 2016/0161315 A1 | 6/2016 | Barty | |

OTHER PUBLICATIONS

Norton S.J. et al., "Mossbauer Imaging", Journal of Research of the National Bureau of Standards, vol. 92, No. 5, Sep.-Oct. 1987, pp. 325-334.

Norton S.J. et al., "Mossbauer Imaging", Nature Publishing Group, vol. 330, No. 12, Nov. 1987, pp. 151-153.

Heeg K.P. et al., "Tunable Subluminal Propagation of Narrow-Band X-Ray Pulses", Physics, Physical Review Letters, PRL 114, 203601 (2015), pp. 203601-1-203601-5.

Kamnev A.A. et al., "Mossbauer Spectroscopy in Biological and Biomedical Research", Mössbauer Spectroscopy: Applications in Chemistry, Biology, and Nanotechnology, First Edition, Chapter 13, 8:10:49, 2013, pp. 272-291.

Chi et al., "Thomson Scattering X-Ray Source: A Novel Tool for Monochromatic Computed Tomography", Proc. SPIE 10391, Developments in X-Ray Tomography XI, 103910Z (Sep. 19, 2017), doi: 10.1117/12.2273136.

Yabashi M. et al., "X-Ray Monochromator with an Energy Resolution of 8=10-9 at 14.41 keV", Review of Scientific Instruments, vol. 72, No. 11, Nov. 2001, pp. 4080-)4083.

* cited by examiner

EXAMINATION OF A BLOOD VESSEL BASED ON NUCLEAR RESONANT ABSORPTION

FIELD OF THE INVENTION

The invention relates to a system and a method for determining at least one characteristic of a portion of a blood vessel of a patient. The characteristic may correspond to a velocity of blood flowing in the portion of the blood vessel. Likewise, the characteristic may correspond to an anatomy of the portion of the blood vessel and/or to a spatial distribution of calcium included therein.

BACKGROUND OF THE INVENTION

A stenosis in a blood vessel can be detected and examined using angiography imaging. In angiography, a contrast agent—typically comprising iodine—is inserted into the blood vessel and the blood vessel is imaged using a suitable imaging modality such as, x-ray imaging, computed tomography (CT) imaging or magnetic resonance (MR) imaging. In the resulting image of the blood flowing through the blood vessel, the stenosis may be detected and its degree may be determined in order to decide about a treatment, such as the insertion of a stent.

However, an anatomical blockage detected in an angiography image might not significantly obstruct the blood flow. As a consequence, unnecessary interventions for stenting patients may be performed, if the decision about the intervention is made on the basis of angiography images alone. Therefore, catheter-based measurements of the blood pressure may be carried out in order to determine whether the blood flow is significantly reduced and whether stenting is necessary. Such measurements have proven to be a reliable means for examining stenosis. However, they are invasive techniques requiring an intervention. Moreover, it can be difficult or impossible to place the measurement catheter in certain blood vessels, and in such cases a measurement might not be possible.

As an alternative, the blood flow through the blood vessel can be determined using computerized blood flow models generated on the basis of angiographic CT images. However, the CT images might be degraded by metal artifacts in case of patients having a pacemaker, an internal defibrillator or a prosthetic heart valve, for example. For such patients, modelling of the blood flow may not be possible.

Furthermore, a stenosis is often caused by calcified plaque in the blood vessel. However, calcium attenuates x-ray radiation similarly as iodine so that it is not possible to distinguish between calcium and iodine in angiographic images. As consequence, angiographic images do not allow for determining the spatial distribution of calcified plaque in a blood vessel including a stenosis.

SUMMARY OF THE INVENTION

In view of this, it is an object of the invention to allow for an improved non-invasive examination of a portion of the blood vessel, particularly in order to characterize a stenosis in the portion of the blood vessel.

In one aspect, the invention suggests a system for determining at least one characteristic of a portion of a blood vessel of a patient, the portion of the blood vessel comprising blood including a contrast agent exhibiting nuclear resonant absorption of x-ray photons at a specific energy. The system comprises: a tunable monochromatic x-ray source configured to emit x-ray radiation, an x-ray detector device arranged to detect the x-ray radiation after it has travelled through the portion of the blood vessel and to provide a detection signal indicative of an intensity of the detected x-ray radiation, and a control unit adapted to vary a tuning of the x-ray source to thereby vary the energy of the x-ray radiation emitted by the x-ray source. Moreover, the system comprises an evaluation unit configured to determine, on the basis of the detection signal, a tuning of the x-ray source at which nuclear resonant absorption of the x-ray radiation incident onto the portion of the blood vessel occurs and to estimate the at least one characteristic on the basis of the determined tuning.

The characteristic may correspond to a velocity of blood flowing in the portion of the blood vessel. In this case, the system allows for determining the blood velocity in a non-invasive procedure. This provides an advantage over the conventional invasive techniques for measuring the blood velocity. In addition, or as alternative, the characteristic may correspond to an anatomy of the portion of the blood vessel and/or to the spatial distribution of calcium included therein. In this respect, the system may particularly produce an angiographic image of the portion of the blood vessel, in which calcium—and, thus, calcified plaque—can be distinguished from other materials, including the contrast agent, so that the spatial distribution of calcium is made visible.

The contrast agent may comprise iodine-127. This substance exhibits a nuclear transition at 57.6 keV giving rise to resonant absorption at the same energy. This energy is in the energy range of x-ray radiation conventionally used for diagnostic purposes in medicine. As a consequence, the system also allows for acquiring diagnostic x-ray images. Moreover, iodine-127 is already in wide use as a contrast agent in radiology so that an approved contrast agent is used in the system.

In one embodiment, the evaluation unit is configured to determine the tuning of the x-ray source at which nuclear resonant absorption of the x-ray radiation incident onto the portion of the blood vessel occurs by determining, on the basis of the detection signal, a tuning of the x-ray source at which a maximum attenuation of the x-ray radiation travelling through the portion of the blood vessel occurs. Since the attenuation of the x-ray radiation is higher in case of nuclear resonance absorption compared with the "normal" interaction between the x-ray radiation and a material, the tuning at which the maximum attenuation of x-ray photons occurs corresponds to the tuning at which nuclear resonant absorption occurs.

Each tuning of x-ray source corresponds to a certain energy of the x-ray radiation emitted by the x-ray source. On the basis of the information about the energy at which nuclear resonant absorption occurs or the corresponding tuning of the x-ray source, the velocity of the blood flowing through the portion of the blood vessel can be determined and on the basis of the detection signal of the x-ray detector acquired at this energy or tuning an angiographic image can be constructed, which allows for distinguishing the contrast agent from calcium.

The determination of the blood velocity in the suggested system relies on the relativistic Doppler shift of the photon energy required for inducing the nuclear resonant absorption, which is caused by the relative motion of the x-ray source and the atomic nuclei of the contrast agent. Since this motion corresponds to the relative motion of the x-ray source and the blood flowing in the examined portion of the blood vessel, the blood velocity can be estimated on the basis of the Doppler shift of the photon energy required for inducing the nuclear resonant absorption with respect to the known transition energy of the nuclear transition corresponding to the nuclear resonant absorption in the rest frame of the nuclei of the contrast agent. Here, the Doppler-shifted photon energy corresponds to a shifted tuning of the x-ray source compared with the tuning at which resonant absorption would occur when the atomic nuclei of the contrast agent were at rest. Thus, the blood velocity can be determined based on the tuning of the x-ray source at which resonant absorption occurs, i.e. the tuning at which the maximum photon attenuation occurs.

In one embodiment, the evaluation unit is further configured to determine the velocity of the blood in the portion of the blood vessel based on an orientation of the portion of the blood vessel. In a related embodiment, the orientation of the blood vessel is determined on basis of a three-dimensional image, particularly a computed tomography image, of the portion of the blood vessel comprising the blood including the contrast agent. Further, in order to take the orientation of the blood vessel into account, the evaluation unit may particularly be configured to determine the velocity of the blood on the basis of an angle between a longitudinal direction of the portion of the blood vessel and a travelling direction of x-ray photons included in the x-ray radiation.

These embodiments take account of the observation that the Doppler shift of the photon energy required for inducing the nuclear resonant absorption also depends on the angle between the travelling direction of the atomic nuclei and the x-ray photons. The travelling direction of the x-ray photons is known in the system from the arrangement of the x-ray source and the x-ray detector. The travelling direction of the atomic nuclei of the contrast agent corresponds to the direction of motion of the blood and this direction corresponds to the orientation of the blood vessel portion to be examined, which can be determined on the basis of a three-dimensional image of the blood vessel portion. In particular, this direction is essentially parallel to the longitudinal axis of the examined portion of the blood vessel. Thus, by determining the blood velocity on the basis of the orientation of the examined portion of the blood vessel and particularly on the basis of the longitudinal axis of the examined blood vessel portion, account can be taken of the dependency of the Doppler shift on the angle between the travelling directions of the atomic nuclei and the x-ray photons.

Moreover, at least in the so called non-relativistic limit, i.e. when the relative velocity of the x-ray source and the atomic nuclei of the contrast agent is small compared with the velocity of light, no Doppler shift of the photon energy occurs if the angle between the travelling direction of the atomic nuclei and the x-ray photons is 90°. Therefore, the patient is preferably positioned relative to the x-ray source such that x-ray photons included in the x-ray radiation travel through the portion of the blood vessel with an angle other than 90° between the travelling direction of the x-ray photons and the longitudinal direction the portion of the blood vessel. This allows for exploiting the relativistic Doppler effect for determining the blood velocity also in case the blood velocity is small compared to the velocity of light, which is usually the case.

The aforementioned three-dimensional image used for determining the orientation of the portion of the blood vessel to be examined may be acquired using another x-ray system, which is configured as a CT system. However, it is likewise possible that the three-dimensional image is acquired using the tunable monochromatic x-ray source and the x-ray detector.

In a related embodiment, the x-ray source and the x-ray detector are moveable relative to the patient such that the x-ray radiation emitted by the x-ray source travels through the portion of the blood vessel under different angles and that the x-ray detector registers projections values of the blood vessel corresponding to the different angles, and the three-dimensional image is generated from the projection values in accordance with a computed tomography reconstruction. In this embodiment, the system itself is enabled for acquiring CT images including the three-dimensional image for determining the orientation of the blood vessel.

Furthermore, the blood velocity varies during the cardiac cycle of the patient and it may be desired to determine the blood velocity in a specific portion of the cardiac cycle. Therefore, one embodiment includes that the system further comprises a gating unit adapted to provide a gating signal for controlling the x-ray source to emit x-ray radiation only during times corresponding to a predetermined portion of a cardiac cycle of the patient. In this embodiment, the measurement of the blood velocity can be carried out with respect to the predetermined portion of the cardiac cycle. The gating signal may be derived from electrocardiogram data.

In an alternative embodiment, the evaluation unit is configured to determine a portion of the cardiac cycle in which a maximum attenuation of the x-ray radiation travelling through the blood vessel occurs. In this embodiment, the measurement can also be carried out continuously—i.e. the x-ray source continuously emits x-ray radiation with a varying photon energy, which is detected in the radiation detector in order to determine the photon energy at which nuclear resonant absorption occurs—and the evaluation unit can retrospectively determine in which portion of the cardiac cycle the maximum attenuation of the x-ray radiation occurred. This determination may be made on the basis of electrocardiogram data acquired during the irradiation of the portion of the blood vessel with x-ray photons.

As said above, the system also allows for determining an image of the portion of the blood vessel showing the anatomy thereof including a spatial distribution of calcium comprised in the portion of the blood vessel. In a related embodiment, the system is configured to produce an x-ray image on the basis of the detector signals acquired at the tuning of the x-ray source at which the maximum attenuation of the x-ray radiation travelling through the blood vessel occurs. In this image, the contrast agent can be distinguished from calcium. While both substances "normally" exhibit similar attenuation properties with respect to x-ray photons so that they cannot be distinguished in conventional x-ray images, the attenuation properties of the contrast agent change when nuclear resonant absorption occurs, i.e. when the maximum attenuation of the x-ray radiation travelling through the blood vessel occurs. Therefore, the image acquired in this embodiment shows the contrast agent and calcium included in the portion of the vessel with different contrasts.

This allows for determining a spatial distribution of calcified plaque in the portion of the blood vessel. Therefore, one embodiment includes that the evaluation unit is configured to determine a position of calcium in the portion of the blood vessel and/or a degree of calcification of the portion of the blood vessel on the basis of the produced image.

In a further aspect, the invention suggests a method for determining at least one characteristic of a portion of a blood vessel of a patient, the portion of the blood vessel including blood comprising a contrast agent exhibiting resonant absorption of x-ray photons at a specific energy. The method comprises (i) controlling a tunable monochromatic x-ray source to emit x-ray radiation, (ii) obtaining a detection signal of an x-ray detector detecting the x-ray radiation after it has travelled through the portion of the blood vessel, (iii) varying a tuning of the x-ray source to thereby vary the energy of the x-ray radiation emitted by the x-ray source, (iv) determining, on the basis of the detection signal, the tuning of the x-ray source at which nuclear resonant absorption of the x-ray radiation incident onto the portion of the blood vessel occurs; and (v) estimating the at least one characteristic on the basis of the determined tuning.

Moreover, the invention suggests a computer program comprising program code for instructing a computer device to perform the method when the program code is executed in the computer device.

It shall be understood that the system of claim 1, the method of claim 14 and the computer program of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
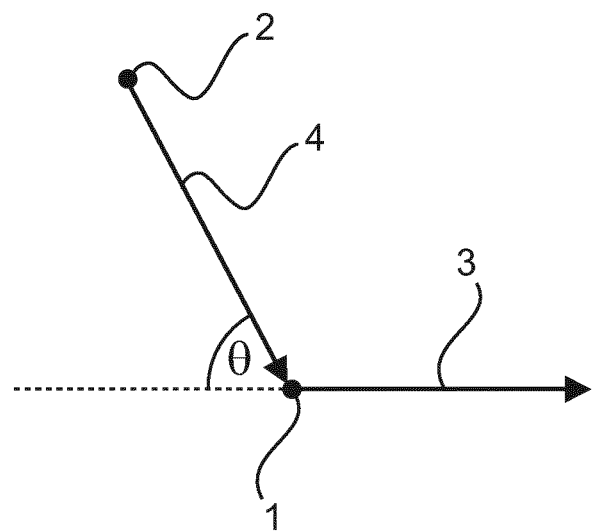
FIG. 1 schematically and exemplarily shows an angle between a direction of motion of an atomic nucleus of a contrast agent and a travelling direction of an x-ray photon, FIG. 2 schematically and exemplarily shows components of a system for determining a characteristic of a blood vessel portion of a patient in one embodiment, FIG. 3 schematically and exemplarily shows components of a system for determining a characteristic of blood vessel portion of a patient in a further embodiment, and FIG. 4 schematically and exemplarily illustrates steps of a method for determining a characteristic of a blood vessel portion of a patient.

The invention suggests determining a velocity of blood flowing in a portion of a blood vessel of a body of a patient based on an excitation of atomic nuclei of a contrast agent introduced into the blood vessel. Moreover, an x-ray image showing plaque, including calcified plaque, in the examined portion of the blood vessel can be acquired in the process of measuring the blood velocity. Thus, two characteristics of a portion of a blood vessel—the blood velocity and the distribution of calcified plaque—can be determined in one measurement, if desired. Likewise, it is possible to either determine the blood velocity or to produce an angiographic image showing the distribution of calcified plaque.

The blood vessel may be a coronary artery in the region of the heart of the patient. However, it is likewise possible to determine the blood velocity in blood vessels in other parts of the body of the patient. The portion of the blood vessel to be examined may have been identified previously, e.g. in an angiographic image, and may include a stenosis that is to be further examined.

The contrast agent is selected such that atomic nuclei included therein exhibit nuclear resonant absorption of x-ray photons at a defined energy. The absorption results in a transition of the atomic nuclei from a non-excited state to an excited state, where the non-excited state and the excited state have an energy difference which is also referred to as transition energy herein. Sometimes this energy is also referred to as Moessbauer energy or Moessbauer line. The invention suggests to exploit the presence of the nuclear resonant absorption for measuring the blood velocity and/or for acquiring angiographic images showing calcified plaque in a blood vessel. The latter is particularly also possible if calcium cannot be distinguished from the contrast agent in "normal" angiographic images—as it is usually the case—because the attenuation of x-ray radiation by the contrast agent changes when x-ray radiation induces the nuclear resonant absorption while the attenuation properties of calcium—which does not exhibit the nuclear transition—are not changed. Therefore, the contrast agent can be distinguished from calcified plaque in images acquired at the photon energy at which nuclear resonant absorption occurs in the contrast agent.

In order for the nuclear resonant absorption to occur, the energy of the x-ray photons in the rest frame of the atomic nuclei has to correspond to the transition energy in order to induce the state transition. If the source emitting the x-ray photons and the atomic nuclei of the contrast agent move relative to each other, the required photon energy in the rest frame of the source shifts as a function of the relative velocity between the source of the x-ray photons and the atomic nuclei due to the relativistic Doppler effect.

On this basis and on the basis of the observation that the velocity of the atomic nuclei of the contrast agent essentially corresponds to the velocity of the blood, the velocity of the blood can be estimated by determining the photon energy at which resonant absorption occurs. For determining this photon energy, the portion of the blood vessel to be examined can be irradiated with x-ray radiation of varying energy by varying the tuning of a tunable monochromatic x-ray source and the tuning associated with the highest photon absorption rate in the contrast agent can be determined. This tuning corresponds to the energy at which resonant absorption occurs in the contrast agent, and on the basis of this tuning the blood velocity in the blood vessel portion can be determined.

If a nucleus is moving with a velocity v at an angle θ between the direction of motion of the nucleus and the travelling direction of an x-ray photon, the photon energy E as seen by the nucleus is given by $$E = E_0 \cdot \frac{1 - v/c \cdot \cos\theta}{\sqrt{1 - v^2/c^2}}$$

where $E_0$ is the energy of the photon emitted by an x-ray source in the reference frame of the x-ray source and c is the speed of light. The angle θ is illustrated in FIG. 1, in which the nucleus is provided with the reference numeral 1, the x-ray source is provided with the reference numeral 2, the direction of motion of the nucleus is provided with the reference numeral 3 and the travelling direction of the x-ray photon with the reference numeral 4. If the velocity v is considerably smaller than the speed of light, as it is the case for the velocity of the blood, the aforementioned formula simplifies in the so-called non-relativistic limit to:

$$E = E_0 \cdot (1 - v/c \cdot \cos\theta)$$

In order to induce the nuclear transition, the energy E has to be equal to the transition energy E of the nuclear transition at rest. In this case and for a given angle θ, the velocity of the atomic nucleus is given in the non-relativistic limit by $$v = \frac{c}{\cos\theta} \cdot \left(1 - \frac{E_{Trans}}{E_{Res}}\right)$$

where $E_{Res}$ denotes the photon energy in the reference frame of the x-ray source for which resonant absorption occurs.

Hence, the velocity of the atomic nuclei of the contrast agent, which corresponds to the velocity of the blood, can particularly be determined based on the energy of x-ray radiation as measured in the rest frame of the x-ray source at which resonant absorption occurs and based on the transition energy of the nuclear transition.

When nuclear resonant absorption occurs, x-ray radiation incident onto the blood is attenuated to an especially high degree, which is particularly higher than the attenuation due to the "normal" interaction of the x-ray radiation with material, i.e. the interaction between the x-ray radiation and the electron shells of the atoms of the material. Hence, the x-ray attenuation, as a function of the energy of the x-ray photons, has a maximum at the energy at which nuclear resonant absorption occurs.

In order to exploit this effect for determining the blood velocity, it is suggested to irradiate the blood using a monochromatic x-ray source and to vary the tuning of the x-ray source to vary the energy of the x-ray photons emitted by the x-ray source. Using an x-ray detector that detects the x-ray radiation traversing the blood, the tuning of the x-ray source at which maximum attenuation of the x-ray radiation occurs may then be determined. This tuning corresponds to the tuning at which the intensity of the x-ray radiation is reduced to the highest degree upon the x-ray radiation has travelled through the blood. On the basis of this tuning and on the basis of the known transition energy of the atomic nuclei of the contrast agent, the blood velocity may be determined, particularly on the basis the aforementioned formulae. For this purpose, the tuning of the x-ray source may be related to the corresponding energy of the x-ray photons so that the blood velocity can be determined in accordance with the aforementioned formulae.

Further, the angle between the direction of motion of the atomic nuclei of the contrast agent is preferably taken into consideration in the determination of the blood velocity. Moreover, this angle is preferably adjusted to a value not equal to 90° because a Doppler shift does not occur in the non-relativistic limit if the angle θ is exactly 90°.

The direction of motion of the atomic nuclei of the contrast agent essentially corresponds to the direction of the blood flow which results from the orientation of the portion of the blood vessel to be examined in space and the direction of the blood flow within this blood vessel portion. For the determination of the blood velocity, it may be assumed that the direction of motion of the atomic nuclei of the contrast agent corresponds to the longitudinal direction of the blood vessel portion, where this direction is parallel to a longitudinal extension of the blood vessel portion and points in the main direction of the blood flow. This longitudinal direction of the blood vessel portion may be determined on the basis of a three-dimensional angiographic image. Therefore, angiographic imaging may likewise be performed in connection with the determination of the blood velocity in order to obtain information about the direction of the blood flow and this information may be used in the determination of the blood velocity.

The contrast agent may particularly include iodine-127. This substance exhibits a nuclear transition with a transition energy of 57.6 keV. The transition has a natural line width of $1.5 \times 10^{-9}$ keV. Therefore, motion of a nucleus with a velocity of 1 cm/s in the travelling direction of the exciting x-ray photons results in a Doppler shift of the photon energy in the range of the natural line width. The blood velocity in a human blood vessel is typically in the range of a few 10 cm/s in case of a healthy blood vessel. Within a stenosis, the blood velocity can reach up to 100-500 cm/s. Thus, a Doppler shift of the photon energy is indeed necessary in order for the x-ray photons to be absorbed by iodine nuclei moving with typical blood velocities. Hence, it is possible to determine the blood velocity on the basis of the excitation of the 57.6 keV transition of iodine-127. Moreover, iodine-127—which is the only stable isotope of natural iodine—is already in wide use as a contrast agent in conventional x-ray based medical imaging. Thus, it is not necessary to approve a new contrast agent.

Likewise, another contrast agent may be used which includes a material having a nuclear transition in a suitable energy range—i.e. in an energy range in which a human body can be irradiated without causing unacceptable detrimental effects—and with a suitably narrow line width.

Figure 2:
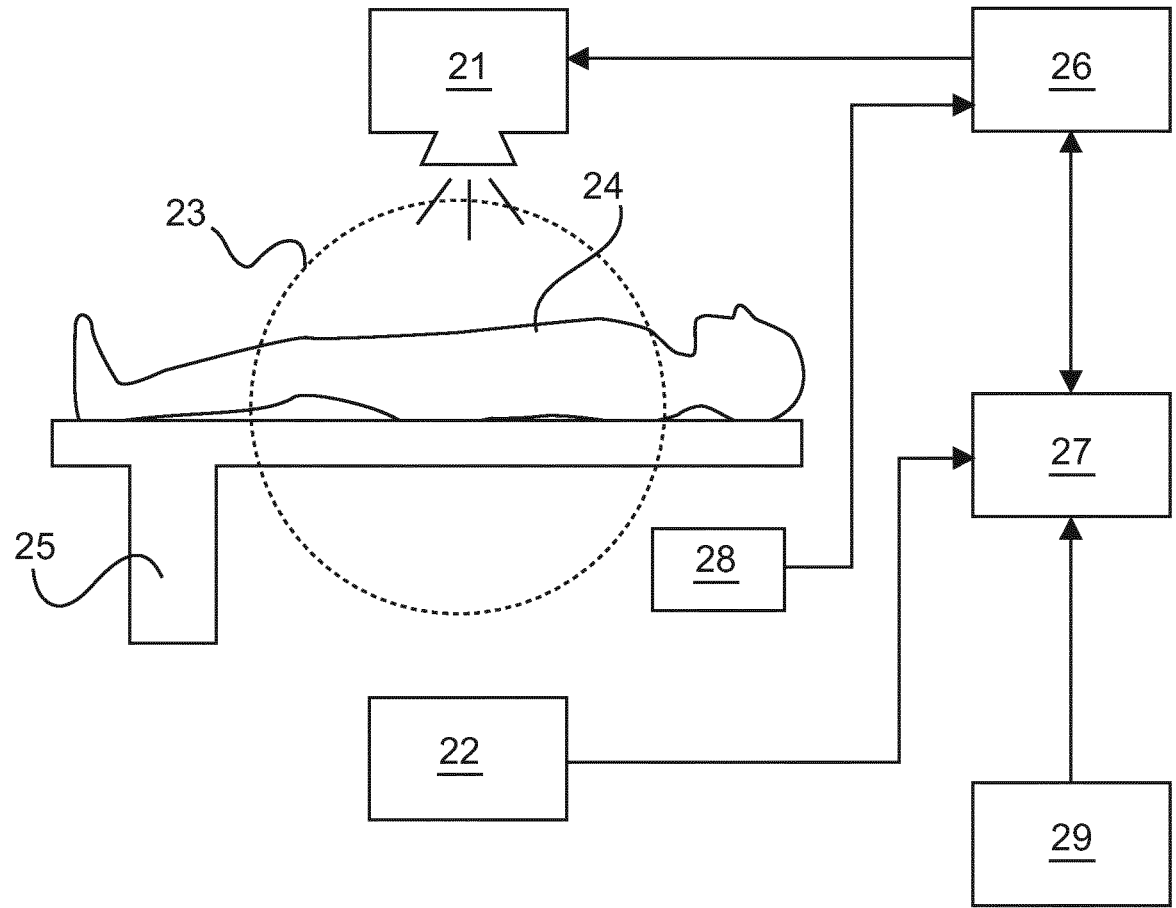

FIG. 2 schematically and exemplarily illustrates components of one embodiment of a system for determining the blood velocity in a selected portion of a blood vessel of a patient. In this embodiment, the system includes an x-ray source 21 and an x-ray detector 22 which are arranged opposite to each other so that x-ray photons emitted by the x-ray source 21 are registered in the x-ray detector 22, if they are not absorbed or deflected on their way from the x-ray source 21 to the x-ray detector 22. Between the x-ray source 21 and the x-ray detector 22, there is a measurement area 23 in which the body 24 of the patient is positioned for examining a portion of a blood vessel of the patient based on nuclear resonant absorption. At least during the measurement, the x-ray source 21 and the x-ray detector 22 are held at a fixed position with respect to the body 24 of the patient in the embodiment illustrated in FIG. 2.

The x-ray source 21 is configured as a tunable monochromatic x-ray source, Thus, the x-ray source 21 emits x-ray photons essentially having a defined energy and this energy can be varied by varying the tuning of the x-ray source 21, where the tuning is characterized by the relevant operation parameters of the x-ray source 21 determining the energy of the emitted x-ray photons. Preferably, the energy bandwidth of the photons in an x-ray beam of a certain nominal energy is not larger than about ten times to 100 times the natural line width of the nuclear resonance transition of the nuclei of the contrast agent. Thus, the energy bandwidth of the x-ray source 21 is preferably in the sub-μeV range.

In order to generate x-ray radiation with a small energy bandwidth in this range and a sufficiently high intensity, the x-ray source 21 may comprise a primary x-ray generator for producing x-ray radiation having a high intensity in a frequency range around the desired output photon energy of the x-ray source 21, and it may additionally comprise an x-ray monochromator for selecting x-ray photons from a sufficiently small part of the energy spectrum of the x-ray photons generated by the primary x-ray generator.

Exemplary primary x-ray generators comprise synchrotrons or free electron lasers generating x-ray radiation in the required energy range in a manner known to a person skilled in the art. A further example is an x-ray generator based on Thomson scattering (also called inverse Compton scattering) of laser pulses from a relativistic electron beam generated by means of a linear electron accelerator. Such an x-ray source is particularly described in Z. Chi et al., "Thomson scattering x-ray source: a novel tool for monochromatic computed tomography", Proc. SPIE 10391, Developments in X-Ray Tomography XI, 103910Z (19 Sep. 2017), doi: 10.1117/12.2273136. Compared to x-ray generators including a synchrotron or a free electron laser, this x-ray generator is more compact and less costly.

The monochromator may be configured as a Si crystal monochromator, for example. Such monochromators allow for producing monochromatic x-ray radiation with an energy resolution $\Delta E/E$ (where $\Delta E$ is the energy bandwidth and E is the photon energy) in the range of $10^{-9}$ keV, which is sufficient to achieve the desired small energy bandwidth for determining the blood velocity. An example of such a monochromator is described in the publication M. Yabashi et al., "X-ray monochromator with an energy resolution of 8×10-9 at 14.41 keV", Review of Scientific Instruments 72, 4080 (2001); https://doi.org/10.1063/1.1406925.

In one implementation, the x-ray source 21 emits x-ray radiation in a diverging x-ray beam. In another implementation, the x-ray source 21 emits an x-ray radiation beam having a parallel beam geometry. For detecting the x-ray radiation, the x-ray detector 22 may comprise a one or two-dimensional detector array including detector elements—so called pixels—for detecting x-ray radiation incident into the detector elements, and for each detector element, the x-ray detector 22 may provide a measurement signal indicating the incident radiation intensity. The x-ray detector 22 may be configured as an indirect conversion detector as known to a person skilled in the art. However, the x-ray detector 22 may likewise be configured in another way, such as for example as a direct conversion detector. The detector array is configured and arranged such that it covers at least a part of the cross section of the x-ray beam emitted by the x-ray source 21 at the position of the x-ray detector 22. Further, the x-ray detector 22 has a defined position relative to the x-ray source 21 so that for each detector element, the connecting lines to the x-ray source 21 are known. These connecting lines correspond to the trajectories of x-ray photons detected in the detector elements after they have travelled in a straight line through the measurement area 23.

In the measurement area 23, the patient body 24 can be positioned on a support 25, and the support 25 may be adjustable in order to positon the patient in such a way that the angle between the longitudinal direction of the blood vessel portion to be examined and the travelling direction of the x-ray photons emitted by the x-ray source differs from 90°. In one related embodiment, the x-ray source 21 and the x-ray detector 22 are arranged such that the x-ray beam emitted by the x-ray source 21 travels in an essentially vertical direction, e.g. in a downward direction, and the patient body 24 is positioned with a suitably inclined longitudinal axis in the measurement area 23 between the x-ray source 21 and the x-ray detector 22. This usually allows for realizing an angle different from 90° between the travelling direction of the x-ray beam and the longitudinal direction of the blood vessels. As an alternative, the x-ray source 21 and the x-ray detector 22 are arranged such that the x-ray beam emitted by the x-ray source travels in an essentially horizontal direction and the patient body 24 may be positioned with its longitudinal axis inclined with respect to the horizontal axis in order to realize an angle different from 90° between the travelling direction of the x-ray beam and the longitudinal direction of the blood vessel to be examined.

The x-ray source 21 is coupled to a control unit 26, which controls the tuning of the x-ray source 21 by controlling the relevant operating parameters of the x-ray source 21, where each tuning corresponds to a certain energy of the x-ray photons emitted by the x-ray source 21. The control unit 26 may also receive a gating signal provided by a gating unit 28 as will be explained herein below and may control the x-ray source 21 in accordance with the gating signal. Moreover, the x-ray detector 22 and the control unit 26 are coupled to an evaluation unit 27. From the x-ray detector 22, the evaluation unit 27 receives a detection signal including information about the intensity of the x-ray radiation detected in the x-ray detector 22, preferably for each detector element individually, and evaluates this detection. From the control unit 26, the evaluation unit 27 receives information indicating the tuning of the x-ray source 21 so that the evaluation unit 27 can associate a radiation intensity measured at a certain time with the tuning of the x-ray source 21 at the same time. In addition, the evaluation unit 27 may receive information about the intensity of the x-ray radiation emitted by the x-ray source 21. Further, the evaluation unit 27 may control the overall operation of the system, and in so doing, it may also control the operation of the control unit 26 associated with the x-ray source 21.

The control unit 26 and the evaluation unit 27 may be configured as computer devices, each comprising a microprocessor programmed for performing the functions provided by the control unit 26 or the evaluation unit 27. For this purpose, a corresponding computer program may be stored and executed in the computer devices. Further, at least the evaluation unit 27 may comprise a suitable user interface for interacting with a user, which may include a display device and suitable input means. Via the user interface, the user may input control commands, e.g. to start the measurement routines provided the system, and may receive outputs of the evaluation unit 27, such as the result of the determination of the blood velocity. Moreover, it is also possible to integrate the control unit 26 and the evaluation unit 27 in one computer device.

Using the aforementioned system, it is possible to determine the velocity of blood flowing through a portion of a blood vessel of the patient and/or to acquire an angiographic image in which the contrast agent is distinguished from calcium including in calcified plaque, as will now be explained in more detail:

In order to determine the blood velocity, the angle between the longitudinal direction of the blood vessel portion to be examined and the travelling direction of the x-ray photons, a three-dimensional is taken into consideration. In order to determine and adjust this angle, an angiographic image of a region of the patient body 24 including the blood vessel portion may be acquired. This image may be acquired using a CT device 29 in manner known to the person skilled in the art. In the CT device 29, the patient body 24 may be supported by a movable support which can is also moved into the measurement area 23 of the system for the blood velocity determination. Thus, the same support 25 may be used for supporting the patient during the acquisition of the angiographic image and for performing the measurements for determining the blood velocity so that the patient does not have to be repositioned between the acquisition of the angiographic image and the measurement of the blood velocity. This ensures that the position and orientation of the blood vessel portion to be examined does not change between the acquisition of the angiographic image and the determination of the blood velocity.

In order to acquire the angiographic image, a suitable contrast agent may be injected into the blood vessel including the portion to be examined, where the contrast agent preferably corresponds to the contrast agent used for determining the blood velocity. Upon having administered the contrast agent, a conventional CT image of the relevant region of the patient body 24 may be acquired by the CT device 29 while the contrast agent flows through the blood vessel.

In the resulting CT image, the blood vessel including the portion to be examined is clearly visible so that the position and the longitudinal direction of this portion can be determined. For this purpose, a blood vessel segmentation may be carried out as known by the person skilled in the art. On the basis of the segmented blood vessel, the position and orientation of the relevant portion thereof may then be determined in a suitable manner. For instance, a middle line of the blood vessel portion may be estimated in order to determine the orientation of the blood vessel portion. In addition, the direction of the blood flow in the blood vessel portion is determined, and on the basis of the orientation of the blood vessel portion and the direction of the blood flow therein, the longitudinal direction of the blood vessel portion is determined. If the blood vessel is curved, the portion thereof which is to be examined, may be selected such that it is approximately straight. In this case, the longitudinal direction of the blood vessel portion can be approximated by the direction of a tangent line to the blood vessel in the region of the selected portion thereof.

Upon having determined the position and the longitudinal direction of the blood vessel portion to be examined, the patient body 24 is positioned in the examination area 23 of the system in order to determine the blood velocity in this portion. Using the information derived from the angiographic CT image, the body 24 of the patient is particularly positioned in such a way that the x-ray beam emitted by the x-ray source 21 travels through the blood vessel portion and that the angle between the longitudinal direction of the blood vessel portion and the travelling direction of the x-ray photons is not equal to 90°. Preferably, the angle is selected as small as possible by suitably positioning the patient body 24 because a smaller angle leads to a larger Doppler shift of the photon energy for inducing nuclear resonant absorption so that the blood velocity can be determined more accurately.

Under the control of the control unit 26, the x-ray source 21 is then operated to irradiate the blood vessel portion with an x-ray beam of varying energy. The energy may be varied in a predetermined range around the transition energy of the nuclei of the contrast agent at rest, where the range may include possible shifted energies necessary in order to induce the nuclear resonance transition when the nuclei of the contrast agent move with a velocity corresponding to typical blood velocities. In order to vary the energy in this range, the tuning of the x-ray source 21 is varied in a corresponding range by varying the relevant operating parameters of the x-ray source 21. Within this range, the tuning may be varied in accordance with a predetermined step size, e.g. by starting with a tuning corresponding to the lowest energy value in the energy range and by adjusting the tuning so that the photon energy increases stepwise.

The x-ray beam emitted by the x-ray source 21 travels through the blood vessel portion and that x-ray photons that have not been absorbed or attenuated are registered in the x-ray detector 22. Usually, several detector elements of the x-ray detector 22 detect x-ray radiation that has travelled through the blood vessel portion. These detector elements may be determined on the basis of the known arrangement of the x-ray source 21 and the x-ray detector 22, the known geometry of the x-ray beam and the position and orientation of the blood vessel portion as determined on the basis of the angiographic CT image.

For each tuning of the x-ray source 21 and for each relevant detector element (i.e. each detector element registering x-ray photons having travelled through the blood vessel portion to be examined), the radiation intensity incident into the detector element is measured in the x-ray detector 22 and forwarded to the evaluation unit 27. For each detector element, the evaluation unit 27 then determines an amount of photon attenuation for the various tunings of the x-ray source 21 and determines the tuning at which the maximum photon attenuation occurred. This tuning corresponds to the energy at which the largest number of photons have been absorbed by the atomic nuclei of the contrast agent and, thus, to the photon energy at which nuclear resonant absorption has occurred.

On the basis of the determined tunings for the different detector elements, the blood velocity is then determined in the evaluation unit 27. For this purpose, the angle between the longitudinal direction of the relevant portion of the blood vessel as determined on the basis of the angiographic image and the travelling direction of the x-ray photons impinging on the x-ray detector 22 is determined for the detector elements. In case the x-ray source 21 emits a diverging x-ray beam, this angle varies for the different detector elements. Therefore, the angle is preferably determined individually for each detector element. In case of a parallel beam geometry, the angle is essentially the same for all detector elements. In this case, one angle can be determined for all detector elements.

For each detector element, the evaluation unit 27 may then determine a value of the blood velocity on the basis of the angle between the longitudinal direction of the blood vessel portion and the travelling direction of the x-ray photons and on the basis of the photon energy for which the minimum intensity has been detected in the detector element. The determination may be made on the basis of the formulae given above taking into consideration the known transition energy of the nuclear transition of the atomic nuclei of the contrast agent. Further, the determination may be made on the basis of the known relationship between the tuning of the x-ray source 21 and the energy of the emitted x-ray photons. One possible procedure for determining this relationship is explained herein below.

From the values of the blood velocity determined for the detector elements receiving x-ray photons having travelled through the portion of the blood vessel to be examined, the evaluation unit 26 may determine a mean value. This may be done at least in case the values do not differ by an amount greater than a threshold so that an essentially homogeneous velocity of the blood in the blood vessel portion may be assumed. This mean value may then be considered as the blood velocity in the blood vessel portion in a further evaluation thereof, e.g. in the diagnosis of a stenosis in the blood vessel portion and in deciding whether a treatment of the stenosis is necessary.

In order to determine the tuning of the x-ray source 21 at which maximum photon attenuation occurs, the x-ray source 21 may be operated to emit x-ray radiation with a constant intensity for all photon energies to which the x-ray source 21 is tuned. In this implementation, the tuning at which maximum photon attenuation occurs is the tuning at which the minimum photon intensity is measured in each detector element.

In an alternative implementation, the emitted photon energy may be determined by comparing, for each tuning of the x-ray source 21, the radiation intensity emitted by the x-ray source 21 with the radiation intensity measured in the x-ray detector 22. On the basis of the difference between these intensities, the evaluation unit 26 determines the photon attenuation for each tuning and for each detector element of the x-ray detector 22. Thereupon, the evaluation 27 may compare the determined photon attenuations to determine the energy at which the maximum photon attenuation occurred to and to estimate the blood velocity on the basis of this energy as described above. In this implementation, the x-ray source 21 does not have be operated to emit radiation with a constant intensity for all photon energies.

The emitted radiation intensity may be estimated on the basis of the respective operating parameters of the x-ray source 21 using a model of the x-ray source 21. Alternatively, the emitted radiation intensity may be measured using an additional x-ray detector, which is arranged to detected x-ray radiation before it reaches the patient body 24. This x-ray detector may particularly be integrated into the x-ray source 21. Moreover, if the x-ray source 21 produces a fan-shaped radiation beam, the additional x-ray detector may be arranged such that it only detects radiation in a small portion of cross section of the x-ray beam. In this portion, the additional x-ray detector may obstruct the x-ray beam but the remaining portion of the x-ray beam may sufficiently illuminate the patient body 24 in order to measure the blood velocity. As an alternative, the additional x-ray detector may be moveable into and out of the x-ray radiation beam. In this implementation, the additional radiation detector may be moved into the radiation beam in order to measure the emitted radiation intensity in at least a part of the cross section of the x-ray beam for each tuning of the x-ray source 21 and then be moved out of the radiation beam again. The patient body 24 may be irradiated before or after this measurement.

Moreover, a calibration of the x-ray source 21 may be required in order to tune the x-ray source 21 precisely to a specific energy and to relate the tunings of the x-ray source 21 to the corresponding photon energies. Therefore, a corresponding calibration measurement may be carried out before the actual measurement of the blood velocity is performed and preferably also before the patient body 24 is positioned in the measurement area 23. In particular, the calibration measurement may be made once in order to calibrate the system for the measurement of the blood velocity for a plurality of patients.

For carrying out the calibration measurement a reference probe including the contrast agent (or the included isotope exhibiting nuclear resonant absorption) may be positioned in the measurement area 23, firstly at a fixed position, i.e. at rest, and irradiated with x-ray radiation. During the irradiation, the x-ray radiation traversing the probe may be detected by means of the x-ray detector 22, and the tuning of the x-ray photons may be varied. The detection signal acquired in this process may be evaluated by the evaluation unit 27 in order to determine the tuning at which the reference probe attenuates the x-ray photons to the maximum degree, where this determination may be made in the same as during the actual measurement described above. This tuning corresponds to a photon energy equal to the transition energy of the atomic nuclei of the contrast agent.

Further, the reference probe may be moved in the measurement area with one or more known velocities in a predefined direction so that there is a known angle between the direction of movement and the travelling direction of the x-ray photons (where this angle may vary for different detector elements in case of a diverging x-ray beam). For each velocity, the tuning of the x-ray source 21 at which maximum photon attenuation occurs may be determined as described above. For this tuning, the corresponding photon energy may then be determined on the basis of the known velocity of the probe, the known angle between the direction of the probe and the travelling direction of the x-ray photons and the known transition energy.

On the basis of these measurements, the relationship between the tuning of the x-ray source 1 and the photon energy may be determined and this relationship may be used in order to determine the blood velocity as explained above. Alternatively, the relationship between the tuning of the x-ray source 1 and the quantity v·cos (θ) may be determined for the relevant contrast agent and the blood velocity may be determined on the basis of this relationship.

In case there is a substantially linear dependence of the photon energy from the tuning, the aforementioned measurements may be made for a resting reference probe and for one velocity and the relationship between the tuning of the x-ray source 21 and the photon energy or the quantity v·cos (θ) for all tunings may be determined on the basis of the determination for this velocity and on the basis of the determination for the resting probe. As an alternative, which may particularly be applied in case the dependency of the photon energy from the tuning is non-linear, the determination may be made for multiple velocities which preferably correspond to possible velocities of blood, and the overall relationship between the tuning of the x-ray source 21 and the photon energy or the quantity v·cos (θ) may be determined based on these determinations in a manner known to a person skilled in the art, e.g. on the basis of a non-linear fitting procedure.

As an alternative to the aforementioned approach, the reference probe may be moved in the measurement area 23 with a varying velocity corresponding to a known velocity profile along a known path (i.e. with known directions). At the same time, the tuning of the x-ray source 21 may be varied such that the attenuation of the x-ray photons constantly remains at its maximum, i.e. such that resonant absorption constantly occurs during the movement. The required variation of the tuning may be controlled by means of a suitable closed-loop regulation. Moreover, the tuning of the x-ray source 21 may be tracked and the relationship between the tuning of the x-ray source 21 and the photon energy or the quantity v·cos (θ) may be determined on the basis of the tracked tuning and the known velocity profile as well as the known path of the motion of the reference probe.

Furthermore, the velocity of the blood flowing through the blood vessel portion to be examined is not constant but varies during a cardiac cycle. In this respect, it may be desired to determine the blood velocity in one selected portion of the cardiac cycle. For this purpose, the measurement of the blood velocity may be carried out at times corresponding to the selected portion of the cardiac cycle. In order to achieve this, the operation of the x-ray source 21 may be gated accordingly. This means that the x-ray source 21 only emits x-ray radiation during the selected portion of the cardiac cycle. For realizing such a gated operation, the system may comprise a gating unit 28, which is adapted to determine the occurrence of predetermined portions of the cardiac cycle. For instance, this determination may be made on the basis of electrocardiography (EKG) data as known to a person skilled in the art. Further, the gating unit 28 outputs a gating signal indicating the times corresponding to the portion of the cardiac cycle selected for determining the blood velocity, and on the basis of this gating signal, the x-ray source 21 may be operated.

If it is desired to determine the blood velocity in several cardiac cycles, separate measurements may be made in each of these cardiac cycles on the basis of corresponding gating signals. Here, each gating signal may indicate the times corresponding to the associated portion of the cardiac cycle, and in each relevant portion of the cardiac cycle the blood velocity may be measured separately as described above.

Likewise, the blood velocity may be measured independent of the cardiac cycle. In this implementation, nuclear resonant absorption will be observed in an arbitrary portion of the cardiac cycle and, thus, the blood velocity in an arbitrary portion cardiac cycle is measured. In order to determine the relevant portion of the cardiac cycle, EKG data may be acquired during the measurement and on the basis of these data, it may be determined in which portion of the cardiac cycle the nuclear resonant absorption occurred during the measurement. In contrast to the gated measurement, this approach allows to carry out the measurement for determining the blood velocity without interruptions.

Figure 3:
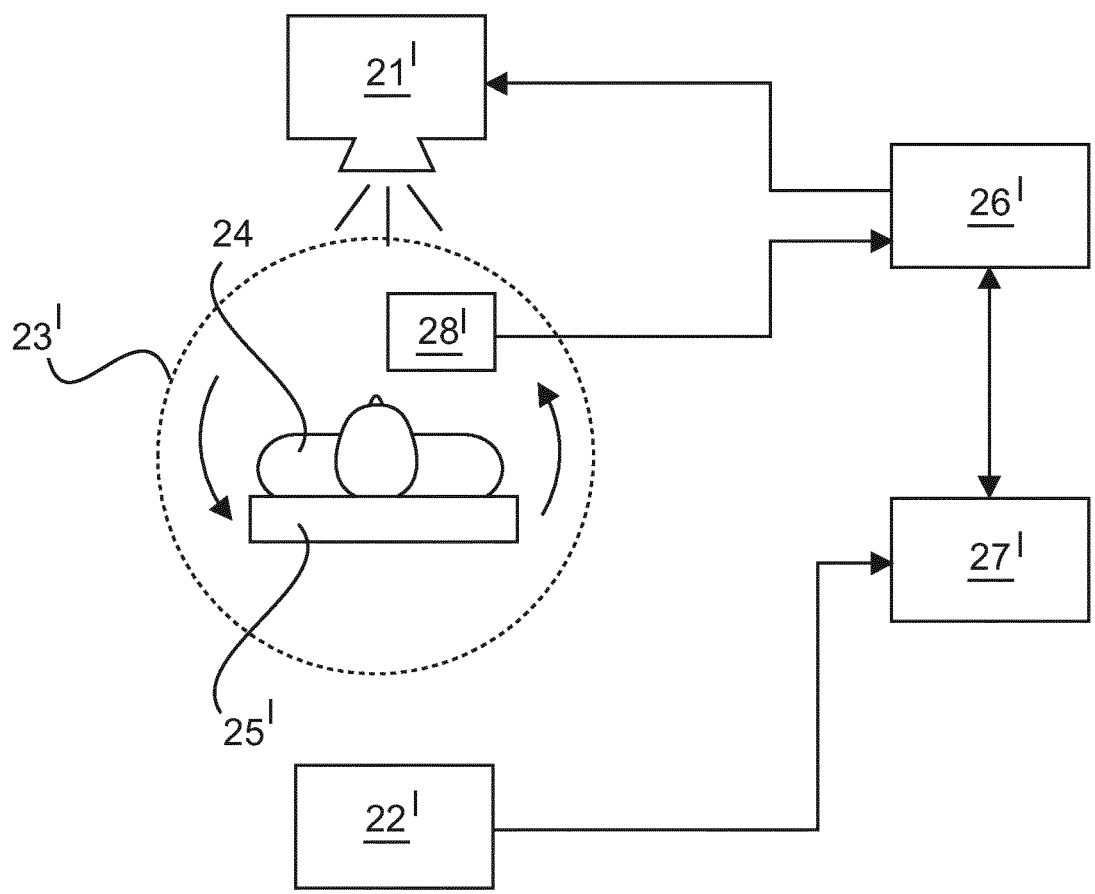

FIG. 3 schematically and exemplarily illustrates components of a system for determining the blood velocity in a further embodiment. This embodiment differs from the embodiment described above in that x-ray source 21' and the x-ray detector 22' can be moved relative to the body 24 of the patient such that x-ray radiation emitted by the x-ray source 21' travels through the body 24 under different angles. This provides improved flexibility in positioning the patient body 24 such that the angle between the longitudinal direction of the blood vessel portion and the travelling direction of the x-ray photons is small. Moreover, it is possible in this embodiment to acquire CT images using the same x-ray source 21' and the same x-ray detector 22' as used for determining the blood velocity.

In one implementation, the x-ray source 21' and the x-ray detector 22' may be mounted on a gantry (not shown in the figure), which can be rotated around the measurement area 23' in which the body 24 of the patient is arranged. In this implementation, the arrangement of the x-ray source 21' and the x-ray detector 22' is similar as in a conventional CT device. The patient body 24 may be positioned in the measurement area 23' in an essentially horizontal position. However, it may also be possible to position the patient body 24 such that its longitudinal axis is inclined with respect to the horizontal direction. In a further implementation, the positions of the x-ray source 21' and the x-ray detector 22' may be fixed and the body 24 of the patient may be rotated in the measurement area 23' in order to acquire a CT image as schematically illustrated in FIG. 3. This implementation also allows to acquire CT images in case an x-ray source 21' is used which is not sufficiently compact for being mounted on a gantry. In this implementation, the body 24 of the patient may be positioned in an essentially upright posture in the measurement area and fixated in such a posture by means of a suitable support 25'. Likewise, the support 25' may be configured such that the patient body 24 can be positioned with its longitudinal axis inclined with respect to the vertical direction.

In both configurations, the x-ray source 21' and the x-ray detector 22' may generally be configured as described in connection with the embodiment illustrated in FIG. 2. Moreover, the x-ray source 21' may again be controlled by a control unit 26', which is particularly configured to vary the tuning of the x-ray source 21' as already described above. In addition, the system may also comprise a gating unit 28' in order to allow for gated x-ray measurements and/or for assigning the measurements to portions of the cardiac cycle of the patient. Moreover, the system again includes an evaluation unit 27' for evaluating the detection signal acquired using the x-ray detector 22'

The aforementioned configurations allow for flexibly positioning the patient body 24 such that the angle between the longitudinal direction of the blood vessel portion to be examined and the travelling direction of the x-ray photons is small as desired for determining the blood velocity. The position and orientation of the blood vessel portion, on the basis of which the patient body 24 is positioned in the measurement area 23' may again be determined on the basis of a three-dimensional angiographic image of the portion of the patient body 24 including the blood vessel portion as described above. The image may be acquired before carrying out the measurement of the blood velocity.

In this respect, it is possible to acquire the three-dimensional angiographic CT image using the x-ray source 21' and the x-ray detector 22' of the system for determining the blood velocity. For acquiring the image, the x-ray source 21' and the x-ray detector 22' are rotated around the body 24 of the patient or the body 24 of the patient is rotated in the measurement area 23' so that the body 24 is irradiated with x-ray radiation emitted by the x-ray source under different angles. For each angle, the x-ray detector 22' registers projection values of the irradiated portion of the body 24 of the patient and on the basis of these projection values a three-dimensional image of the body portion is generated by means of a CT reconstruction procedure as known by a person skilled in the art.

The determination of the blood velocity may then be carried out in the same way as described above in connection with the system illustrated in FIG. 2. In particular, the determination may be made using a suitable relative positioning of the blood vessel portion and the x-ray source 21' as well as the x-ray detector 22'. For the determination, the tuning of the x-ray source 21' may be varied by the control unit 26' and on the basis of the detection signal acquired by means of the x-ray detector 22', an evaluation unit 27' may determine the tuning at which the maximum photon attenuation occurs and may estimate the blood velocity based on this tuning as explained above. Using a gating signal provided by the gating unit 28', the determination may again be performed with respect to one or more specific portion(s) of the cardiac cycle of the patient.

In further embodiments, an angiographic image is acquired which shows the contrast agent and calcified plaque with different contrasts so that the spatial distribution of calcified plaque in the examined blood vessel portion can be determined. The image may be acquired using a system as explained above at the tuning of the x-ray source 21, 21' at which nuclear resonant absorption occurs. In this situation, the contrast agent attenuates x-ray photons to a higher degree than in situations in which no nuclear resonant absorption occurs. Thus, the contrast agent exhibits a higher photon attenuation than the calcium included in the calcified plaque, which "normally" (i.e. when no nuclear resonant absorption occurs) has similar attenuation properties as the contrast agent.

In one implementation, the angiographic image is acquired during the measurement of the blood velocity in the examined blood vessel portion. In this embodiment, the image is produced using the detection signal of the x-ray detector 22, 22' acquired for the tuning of the x-ray source 21 at which nuclear resonant absorption occurs. Using this detection signal, the angiographic image can be produced in a conventional manner as known to a person skilled in the art.

If the x-ray source 21, 21' emits a diverging x-ray beam, the photon energy at which nuclear resonant absorption occurs may be different for the individual detector elements of the x-ray detector 22, 22' due to the varying angle between travelling direction of the x-ray photons registered in the detector elements and the travelling direction of the blood or contrast agent. In this case, the selection of the detection signal for constructing the angiographic image may be made for each detector element individually and the angiographic image may then be constructed from this selected detection signal. Thus, the image may be generated from detection signals of the individual detector elements, which are acquired at different points in time. In order to still generate an angiographic image having a uniform contrast, the x-ray source 21, 21' may be operated to emit x-ray radiation at a constant intensity for all photon energies, or intensity differences may be corrected in the process of reconstructing the image.

In case of a parallel beam geometry, the angle between travelling direction of the x-ray photons registered in the detector elements and the travelling direction of the blood or contrast agent, which essentially corresponds to the longitudinal direction of the examined blood vessel portion, is essentially the same for all detector elements. Thus, in case of a parallel beam geometry, the image may be generated from detection signals of the detector elements, which are acquired simultaneously at the same point in time.

This provides an advantage over conventional digitized subtraction angiography, which is conventionally used in order to make calcifications of a blood vessel visible. In this approach, a first image of the blood vessel is acquired before the contrast agent is injected into the blood vessel, where in this image calcified plaque is visible. The first image is then subtracted from a second image of the blood vessel, which is acquired upon having injected the contrast agent into the blood vessel. Hereby, a difference image can be produced which only shows the contrast agent. However, since the two images are acquired at different points in time and the blood vessel may move between these points in time, the difference image may include motion artifacts. This is particularly true for blood vessels near the heart. These motion artifacts can be avoided by acquiring an image showing calcified plaque on the basis of the detection signal measured at a single point in time as described above.

In a further variant, the angiographic image is acquired without a simultaneous determination of the blood velocity. In this implementation, the detection signal for generating the angiographic image likewise correspond to the detection signal acquired at the tuning of the x-ray source 21, 21' at which nuclear resonant absorption occurs and this detection signal is acquired as described above. Thus, the blood vessel portion to be examined is irradiated with x-ray radiation and tuning of the x-ray source 21, 21' may be varied to vary the energy of the x-ray photons. Then, the tuning at which resonant absorption occurs is determined as described above for each detector element of the x-ray detector 22, 22' and the detection signals of the detector elements acquired at these tunings are selected for constructing the angiographic image.

However, while the patient body 24 is positioned such that the angle between the longitudinal axis of the examined blood vessel portion and the travelling direction of the x-ray photons differs from 90° in order to determine the blood velocity, such a positioning is not necessary in order to acquire the angiographic image because the acquisition of this image is independent from the relativistic Doppler effect. In fact, no knowledge of the angle between the longitudinal axis of the examined blood vessel portion and the travelling direction of the x-ray photons is needed in order to generate the angiographic image. Rather it is sufficient to tune the x-ray source 21, 21' to the x-ray photon energy at which nuclear resonant absorption occurs and to construct the angiographic image on the basis of the detection signal acquired at this tuning.

In the aforementioned manner, a two-dimensional angiographic image of the examined blood vessel portion can be generated. In a variant of the aforementioned implementations, it is also possible to acquire a three-dimensional angiographic image of the blood vessel portion. For this purpose, the detection signal for generating the image may be acquired in a way described above under several angles between the x-ray beam and the patient body 24 in order to reconstruct a CT image of the blood vessel portion. This may be done using the x-ray system illustrated in FIG. 3.

In the embodiments described above, a characteristic of a portion of a blood vessel of a patient can be determined on the basis of nuclear resonant absorption. As explained, the characteristic may be the velocity of the blood flowing through the blood vessel portion. Likewise, the characteristic may be the anatomy of the blood vessel portion and/or a spatial distribution of calcium included therein.

Figure 4:
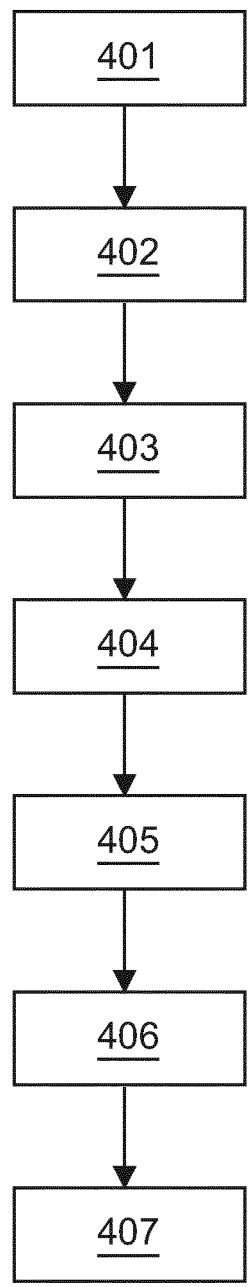

FIG. 4 systematically and exemplarily shows steps performed in the systems according to the aforementioned embodiments to determine the relevant characteristic of the blood vessel portion: Upon having properly positioned the patient body 24 in the measurement area 23, 23' of the used system in step 401, the x-ray measurements for determining the desired characteristic of the blood vessel portion may be started. During the measurements, the control unit 26, 26' may control the x-ray source 21, 21' to emit x-ray radiation irradiating the blood vessel portion to be examined in step 402. During the irradiation of the blood vessel portion, the control unit 26, 26' varies the tuning of the x-ray source 21, 21' to thereby vary the energy of the x-ray radiation emitted by the x-ray source 21, 21' (step 403). After the x-ray radiation has travelled through the blood vessel portion, it is detected by means of the x-ray detector 22, 22' of the system (step 404). The detection signal of the x-ray detector 22, 22' is provided to the evaluation unit 27, 27' of the system in step 405. On the basis of the detections signal obtained in this step, the evaluation unit 27, 27' determines the tuning of the x-ray source 21, 21' at which the maximum attenuation of the x-ray radiation travelling through the portion of the blood vessel occurs (step 406). On the basis of the determined tuning, the evaluation unit 27, 27' then determines the desired characteristic of the blood vessel portion as explained above (step 407).

Variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A computer program may be stored/distributed on a suitable medium, such as an optical storage medium or a solid-state medium, supplied together with or as part of other

The invention claimed is:

1. A system for determining at least one characteristic of a portion of a blood vessel, the system comprising:
   a tunable monochromatic x-ray source configured to emit x-ray radiation;
   an x-ray detector configured to detect the x-ray radiation after travelling through the portion of the blood vessel and provide a detection signal indicative of an intensity of the detected x-ray radiation, the portion of the blood vessel comprising blood including a contrast agent exhibiting nuclear resonant absorption of x-ray photons;
   a controller configured to vary a tuning of the x-ray source thereby varying energy of the x-ray radiation emitted by the x-ray source; and
   an evaluation unit configured to determine, based on the detection signal, the tuning of the x-ray source at which nuclear resonant absorption of the x-ray radiation incident onto the portion of the blood vessel occurs and estimate the at least one characteristic based on the determined tuning.

2. The system as defined in claim 1, wherein the contrast agent comprises iodine-127.

3. The system as defined in claim 1, wherein the evaluation unit is configured to determine the tuning of the x-ray source at which nuclear resonant absorption of the x-ray radiation incident onto the portion of the blood vessel occurs by determining, based on the detection signal, the tuning of the x-ray source at which a maximum attenuation of the x-ray radiation travelling through the portion of the blood vessel occurs.

4. The system as defined in claim 1, wherein the at least one characteristic of the portion of the blood vessel comprises a velocity of the blood flowing in the portion of the blood vessel.

5. The system as defined in claim 4, wherein the evaluation unit is further configured to determine the velocity of the blood in the portion of the blood vessel based on an orientation of the portion of the blood vessel.

6. The system as defined in claim 5, wherein the orientation of the blood vessel is determined based on a three-dimensional image of the portion of the blood vessel comprising the blood including the contrast agent.

7. The system as defined in claim 4, wherein the evaluation unit is further configured to determine the velocity of the blood based on an angle between a longitudinal direction of the portion of the blood vessel and a travelling direction of x-ray photons included in the x-ray radiation.

8. The system as defined in claim 4, wherein x-ray photons included in the x-ray radiation travel through the portion of the blood vessel with an angle other than 90° between a travelling direction of the x-ray photons and a longitudinal direction of the portion of the blood vessel.

9. The system as defined in claim 6, wherein the x-ray source and the x-ray detector are moveable such that the x-ray radiation emitted by the x-ray source travels through the portion of the blood vessel under different angles and that the x-ray detector registers projections values of the blood vessel corresponding to the different angles, and wherein the three-dimensional image is generated from the projection values in accordance with a computed tomography reconstruction.

10. The system as defined in claim 3, further comprising a gating unit adapted to provide a gating signal for controlling the x-ray source to emit x-ray radiation only during times corresponding to a predetermined portion of a cardiac cycle of the patient.

11. The system as defined in claim 1, wherein the characteristic of the portion of the blood vessel comprises an anatomy thereof and/or a spatial distribution of calcium included in the portion of the blood vessel.

12. The system as defined in claim 11, further configured to produce an x-ray image based on the detection signal acquired at the tuning of the x-ray source at which the maximum attenuation of the x-ray radiation travelling through the blood vessel occurs.

13. The system as defined in claim 12, wherein the evaluation unit is configured to determine a position of calcium in the portion of the blood vessel and/or a degree of calcification of the portion of the blood vessel based on the produced x-ray image.

14. A computer-implemented method for determining at least one characteristic of a portion of a blood vessel, the method comprising:
   controlling a tunable monochromatic x-ray source to emit x-ray radiation;
   detecting the x-ray radiation after travelling through the portion of the blood vessel, wherein the portion of the blood vessel comprises blood including a contrast agent exhibiting nuclear resonant absorption;
   varying a tuning of the x-ray source, thereby varying energy of the x-ray radiation emitted by the x-ray source;
   determining, based on the detection signal, the tuning of the x-ray source at which nuclear resonant absorption of the x-ray radiation incident onto the portion of the blood vessel occurs; and
   estimating the at least one characteristic based on the determined tuning.

15. A non-transitory computer-readable medium having executable instructions stored thereon which, when executed by at least one processor, cause the at least one processor to perform a computer-implemented method for determining at least one characteristic of a portion of a blood vessel, the method comprising:
   controlling a tunable monochromatic x-ray source to emit x-ray radiation;
   detecting the x-ray radiation after travelling through the portion of the blood vessel, wherein the portion of the blood vessel comprises blood including a contrast agent exhibiting nuclear resonant absorption;
   varying a tuning of the x-ray source, thereby varying energy of the x-ray radiation emitted by the x-ray source;
   determining, based on the detection signal, the tuning of the x-ray source at which nuclear resonant absorption of the x-ray radiation incident onto the portion of the blood vessel occurs; and
   estimating the at least one characteristic based on the determined tuning.

* * * * *